United States Patent
Kuyler et al.

(10) Patent No.: US 11,596,524 B2
(45) Date of Patent: Mar. 7, 2023

(54) EXPANDING INTERBODY IMPLANT AND METHOD

(71) Applicant: WARSAW ORTHOPEDIC INC., Warsaw, IN (US)

(72) Inventors: Adriaan J. Kuyler, Saint Augustine, FL (US); Anthony J. Melkent, Germantown, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 341 days.

(21) Appl. No.: 16/938,088

(22) Filed: Jul. 24, 2020

(65) Prior Publication Data
US 2022/0023062 A1    Jan. 27, 2022

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2002/30411* (2013.01); *A61F 2002/443* (2013.01)

(58) Field of Classification Search
CPC .................. A61F 2/4425; A61F 2/4455; A61F 2002/30411; A61F 2002/443
See application file for complete search history.

(56) References Cited

U.S. PATENT DOCUMENTS

| | | | |
|---|---|---|---|
| 6,176,882 B1 * | 1/2001 | Biedermann | A61F 2/447 623/17.11 |
| 8,366,777 B2 | 2/2013 | Matthis et al. | |
| 9,216,095 B2 | 12/2015 | Glerum et al. | |
| 9,962,272 B1 | 5/2018 | Daffinson et al. | |
| 10,085,846 B2 | 10/2018 | Grotz | |
| 10,226,359 B2 * | 3/2019 | Glerum | A61F 2/4611 |
| 10,888,431 B1 * | 1/2021 | Robinson | A61F 2/4611 |
| 10,973,649 B2 * | 4/2021 | Weiman | A61F 2/4465 |
| 11,065,127 B1 | 7/2021 | Lentner et al. | |
| 2013/0158664 A1 * | 6/2013 | Palmatier | A61F 2/4425 623/17.16 |
| 2015/0272743 A1 * | 10/2015 | Jimenez | A61F 2/447 623/17.16 |
| 2016/0166396 A1 * | 6/2016 | McClintock | A61F 2/447 623/17.16 |
| 2017/0112630 A1 * | 4/2017 | Kuyler | A61F 2/4455 |

(Continued)

*Primary Examiner* — Nicholas J Plionis
(74) *Attorney, Agent, or Firm* — Sorell, Lenna & Schmidt, LLP

(57) ABSTRACT

A device includes a core having proximal and distal ends and defining a first female thread. A drive screw includes first and second ends. The first end includes a first male thread. The second end including a second male thread that engages the first female thread. A first body includes a second female thread that engages the first male thread. A second body is coupled to the drive screw. A first plate is coupled to the core and the first body. The first plate includes a first vertebral engaging surface. A second plate is coupled to the core and includes a second vertebral engaging surface. The drive screw is configured to rotate relative to the core to simultaneously pivot the first plate relative to the core and alter a distance between the first vertebral engaging surface and the second vertebral engaging surface.

20 Claims, 3 Drawing Sheets

(56) References Cited

U.S. PATENT DOCUMENTS

| | | | |
|---|---|---|---|
| 2017/0128226 A1* | 5/2017 | Faulhaber | A61F 2/30767 |
| 2017/0216045 A1* | 8/2017 | Dewey | A61F 2/4611 |
| 2019/0105178 A1 | 4/2019 | May et al. | |
| 2020/0281741 A1* | 9/2020 | Grotz | A61F 2/447 |

* cited by examiner

EXPANDING INTERBODY IMPLANT AND METHOD

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

In one embodiment, in accordance with the principles of the present disclosure, a device to space apart vertebral members includes a core extending along a longitudinal axis between opposite proximal and distal ends. The core defines a first female thread. A drive screw includes opposite first and second ends. The first end includes a first male thread. The second end includes a second male thread. The second male thread engages the first female thread. A first body comprises a second female thread. The first body is coupled to the first end such that the first male thread engages the second female thread. A second body is coupled to the drive screw. A first plate is coupled to the core and the first body. The first plate comprises a first vertebral engaging surface. A second plate is coupled to the core. The second plate comprises a second vertebral engaging surface. The drive screw is configured to rotate relative to the core to simultaneously pivot the first plate relative to the core and alter a distance between the first vertebral engaging surface and the second vertebral engaging surface.

In one embodiment, in accordance with the principles of the present disclosure, a device to space apart vertebral members includes a core extending along a longitudinal axis between opposite proximal and distal ends. The core defines a first female thread. A drive screw includes opposite first and second ends. The first end includes a first male thread. The second end includes a second male thread. The second male thread engages the first female thread. A first body comprises a second female thread. The first body is coupled to the first end such that the first male thread engages the second female thread. A second body is coupled to the drive screw. A first plate is coupled to the core and the first body. The first plate comprises a first vertebral engaging surface. A second plate is coupled to the core. The second plate comprises a second vertebral engaging surface. The drive screw is configured to rotate relative to the core to simultaneously pivot the first plate relative to the core and alter a distance between the first vertebral engaging surface and the second vertebral engaging surface. The first body comprises a first ramp. The first plate comprises a second ramp. The second ramp is configured to slide along the first ramp to pivot the first plate relative to the core. The second plate comprises a plurality of first inclined surfaces. The second body comprises a plurality of second inclined surfaces. The second inclined surfaces are configured to slide along the first inclined surfaces to alter the distance between the first vertebral engaging surface and the second vertebral engaging surface.

In one embodiment, in accordance with the principles of the present disclosure, a device to space apart vertebral members includes a core extending along a longitudinal axis between opposite proximal and distal ends. The core defines a first female thread. A drive screw includes opposite first and second ends. The first end includes a first male thread. The second end includes a second male thread. The second male thread engages the first female thread. A first body comprises a second female thread. The first body is coupled to the first end such that the first male thread engages the second female thread. A second body is coupled to the drive screw. A first plate is coupled to the core and the first body. The first plate comprises a first vertebral engaging surface. A second plate is coupled to the core. The second plate comprises a second vertebral engaging surface. Rotation of the drive screw relative to the core in a first direction moves the device from a first configuration in which the vertebral surfaces extend parallel to the longitudinal axis and are spaced apart from one another by a first distance to a second configuration in which the first vertebral surface extends at an acute angle relative to the longitudinal axis and the vertebral surfaces are spaced apart from one another by an increased second distance.

BRIEF DESCRIPTION OF THE DRAWINGS

The present disclosure will become more readily apparent from the specific description accompanied by the following drawings, in which.

DETAILED DESCRIPTION

Figure 1:
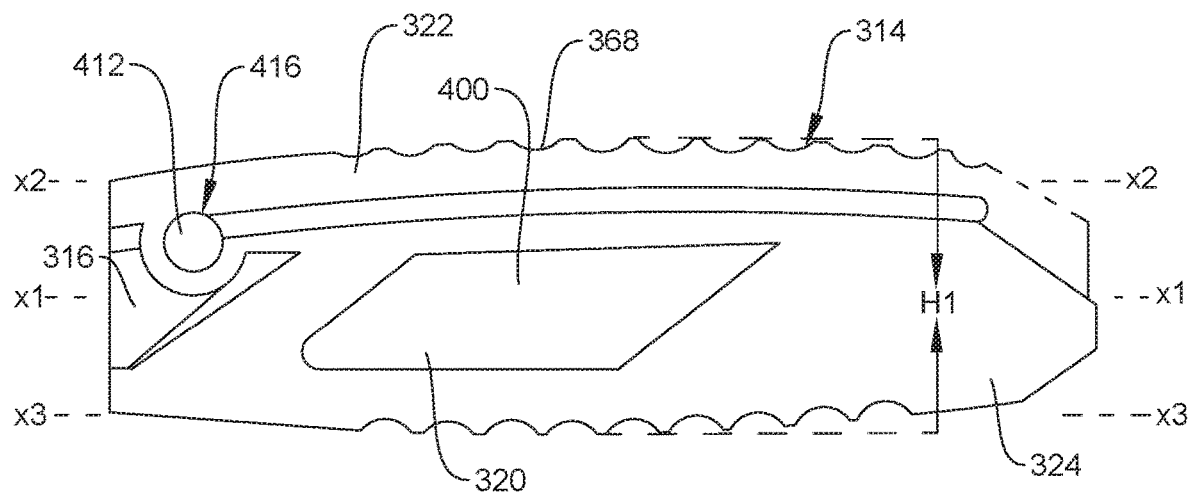
FIG. 1 is a side view of one embodiment of an implant of a system in accordance with the principles of the present disclosure.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates.

In some embodiments, the expandable interbody implant of the system disclosed herein is used to achieve implanted geometries that would otherwise be impossible or challenging to insert with minimal morbidity. The expandable interbody implant allows for expansion in two manners. One component increases the overall height of the implant (parallel expansion), while another manipulates the angle of the implant simultaneously as the other component increases the overall height of the implant.

In some embodiments, the parallel and angular expansion are both infinitely adjustable (within the prescribed range). In some embodiments, the implant is configured to cover all clinically needed size combinations (angles and heights) with a single implant. In some embodiments, the implant is post-packed with bone graft.

It is envisioned that the implant provides the ability to closely match a patient's disc geometry since any height and angle combination of the implant is attainable. Since only one or a few different size implants would be needed to match any disc geometry, manufacturing costs could be significantly reduced, leaning out production and logistics. There is also a reduced number of instruments that would be required for implantation of the implant(s). The system of the present disclosure may also prevent the need to have trials or distractors because of the capabilities of the implant of the present disclosure, which would also reduce the traditional surgical steps.

In some embodiments, the expandable interbody implant of the system disclosed herein includes a single screw to allow for an increase in graft volume as the device is expanded. The implant includes left hand threads that engage screw to allow the first part to advance faster than the second part.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of an interbody implant system 300 in accordance with the principles of the present disclosure.

The components of system 300 can be fabricated from biologically acceptable materials suitable for medical applications, including metals, synthetic polymers, ceramics and bone material and/or their composites, depending on the particular application and/or preference of a medical practitioner. For example, the components of system 300, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaprolactone and their combinations. Various components of system 300 may be fabricated from material composites, including the above materials, to achieve various desired characteristics such as strength, rigidity, elasticity, flexibility, compliance, biomechanical performance, durability and radiolucency or imaging preference. The components of system 300, individually or collectively, may also be fabricated from a heterogeneous material such as a combination of two or more of the above-described materials.

System 300 can be employed in fusion and fixation procedures, for example, for patients suffering from a spinal disorder to provide height restoration between vertebral bodies, decompression, restoration of sagittal balance and/or resistance of subsidence into vertebral endplates. The components of system 300 may be monolithically formed, integrally connected or include fastening elements and/or instruments, for example, as described herein.

System 300 includes an implant, such as, for example, an intervertebral implant 314. Implant 314 is configured for simultaneous parallel and angled expansion, as discussed herein. Implant 314 is configured to be positioned within an intervertebral space wherein the height and angle of implant 314 can be selectively increased and/or decreased with implant 314 in the intervertebral space. The height and angle of implant 314 are increased and/or decreased simultaneously. That is, the height of implant 314 cannot be increased or decreased without also increasing in or decreasing the angle of implant 314, and vice versa.

Implant 314 includes a core 316, a member 318, a member 320, a plate 322 and a plate 324. Implant 314 further includes a drive screw 326 having a male thread 328 configured to mate with a female thread 330 of member 318 and a male thread 332 configured to mate with a female thread 334 of core 316 such that rotation of screw 326 relative to core 316 and member 318 translates members 318, 320 in a first along a longitudinal axis X1 to simultaneously increase and/or decrease the angle and height of implant 314. Screw 326 includes an unthreaded portion 336 that extends through an opening of member 320 such that screw 326 is rotatable relative to member 320 to translate member 320 along axis X1 in the directions shown by arrows A and B in FIG. 3 as the angle and height of implant 314 are simultaneously increased and/or decreased.

In some embodiments, at least one of threads 328, 330, 332, 334 is a right-handed thread and at least one of threads 328, 330, 332, 334 is a left-handed thread. In some embodiments, threads 328, 330 are right-handed threads and threads 332, 334 are left-handed threads to allow member 318 to advance faster than member 320 when screw 326 rotates relative to core 316 and member 318 to translate members 318, 320 together in opposite directions along axis X1, as discussed herein. In some embodiments, threads 328, 330 are opposite-handed threads from threads 332, 334 to allow member 318 to advance faster than member 320 when screw 326 rotates relative to core 316 and member 318 to translate members 318, 320 together in opposite directions along axis X1, as discussed herein.

Figure 3:
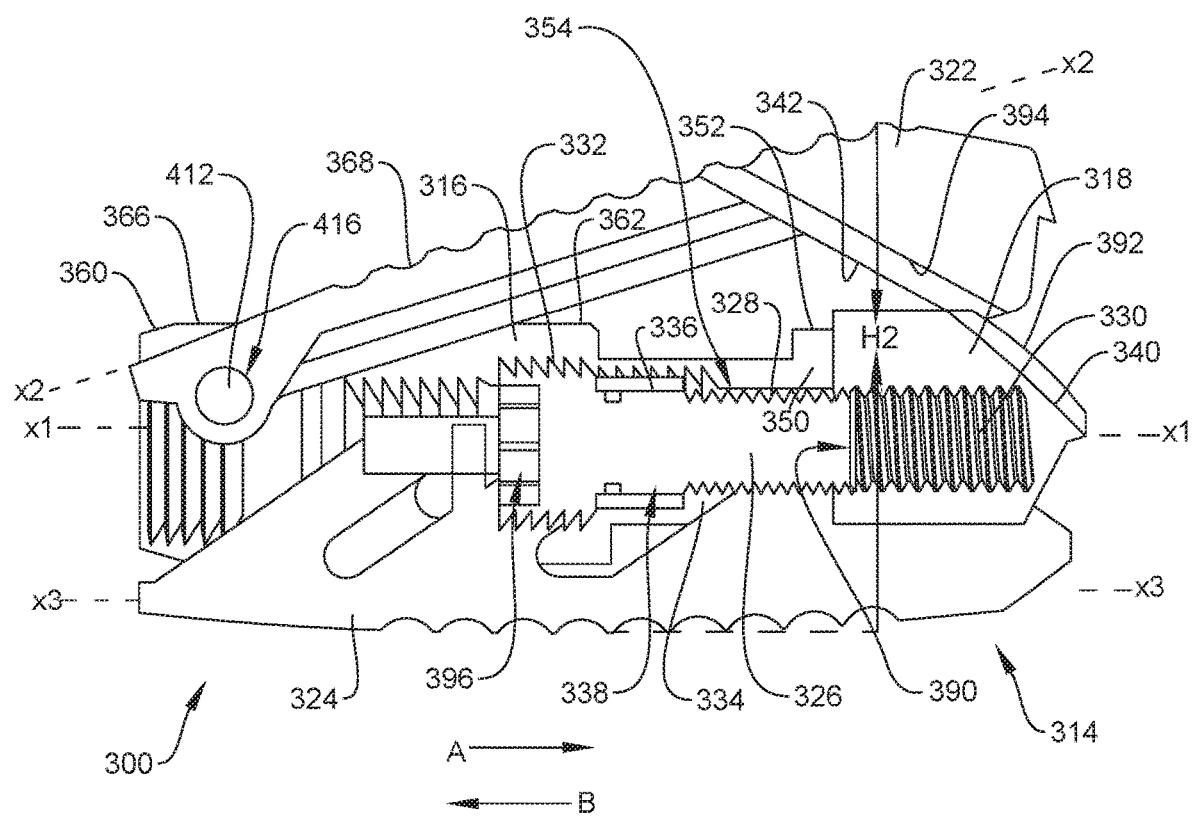
FIG. 3 is a side, cross-sectional view of the implant shown in FIG. 1.
Figure 4:
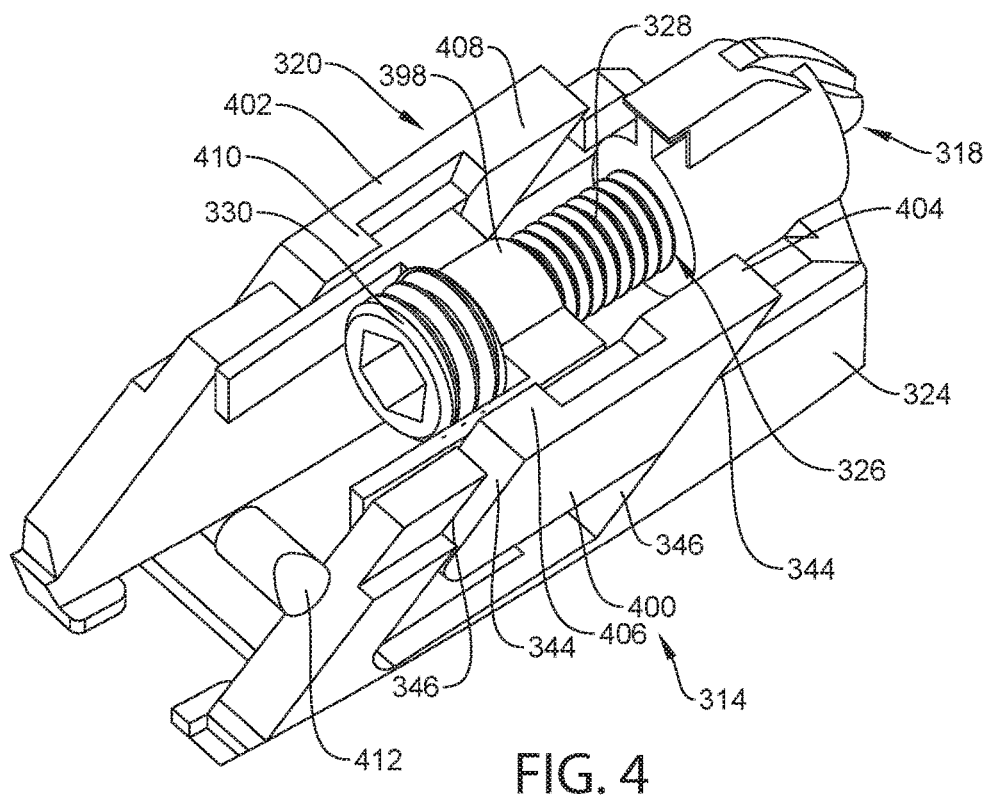
FIG. 4 is a perspective view, in part phantom, of the implant shown in FIG. 1.
Figure 5:
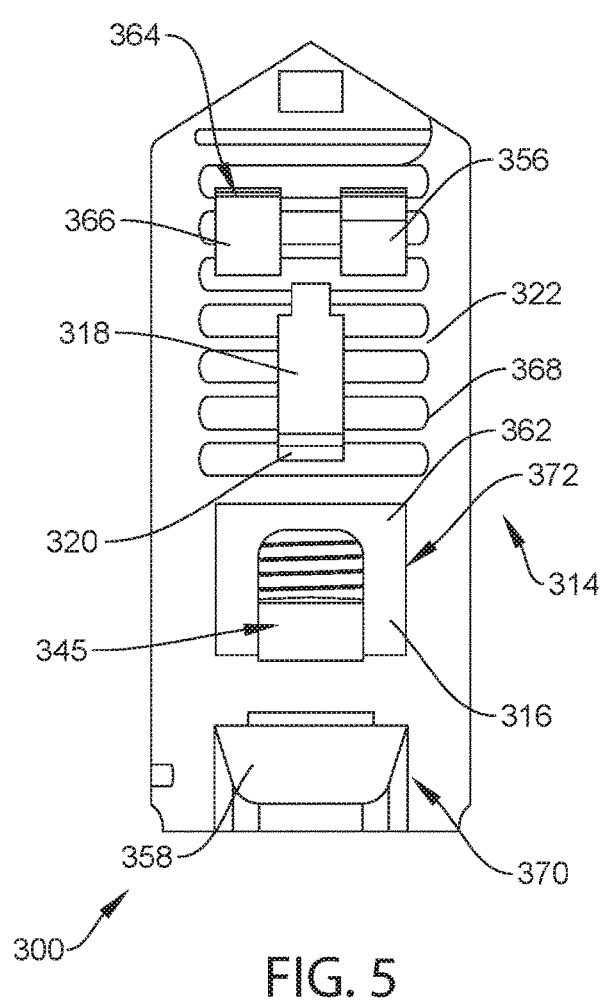
FIG. 5 is a top view of the implant shown in FIG. 1.
Figure 6:
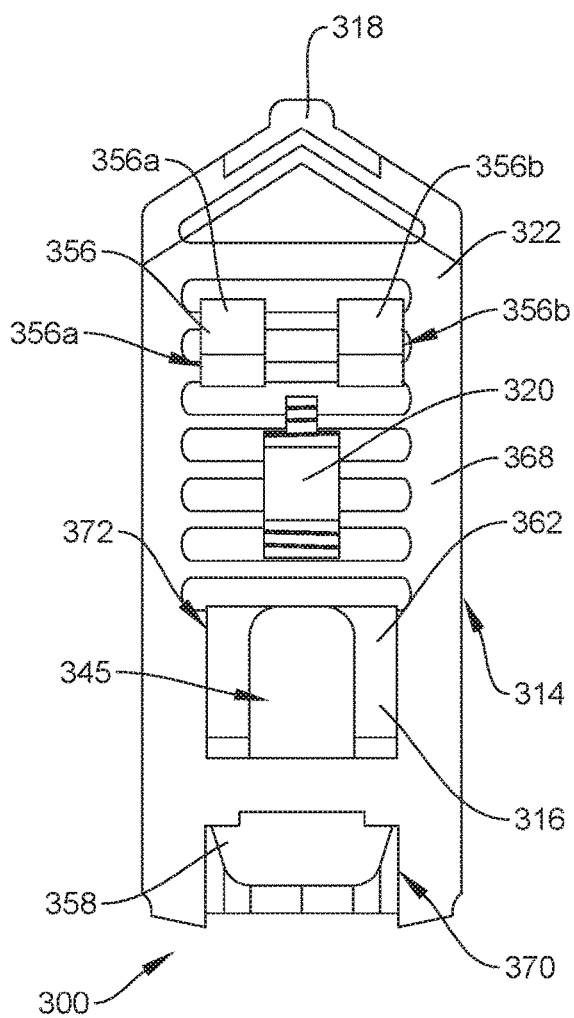
FIG. 6 is top view of the implant shown in FIG. 1.

As screw 326 is rotated about axis X1 in a first rotational direction, screw 326 translates along axis X1 in the direction shown by arrow A in FIG. 3 such that member 318 moves along axis X1 in the direction shown by arrow A in FIG. 3 and member 320 translates along axis X1 in the direction shown by arrow A in FIG. 3, a surface or ramp 340 of member 318 slides along a surface or ramp 342 of plate 322 and inclined surfaces 344 of member 320 slide along inclined surfaces 346 of plate 324 to simultaneously increase the angle of implant 314 and the height of implant 314. In some embodiments, a cavity 345 of implant 314 that is configured for disposal of material, such as, for example, bone graft material has a first volume v1 before the angle and height of implant 314 is increased, as shown in FIG. 5, and an increased second volume v2 after the angle and height of implant 314 is increased, as shown in FIG. 6. In some embodiments, plate 322 is coupled to core 316 by a pin 412 that extends through an opening 414 in core 316 and an opening 416 in plate 322 such that plate 322 is pivotable relative to core 316 about pin 412. In some embodiments, opening 414 includes spaced apart first and second openings 414, opening 416 includes a first opening 416 that is aligned with the first opening 414 and a second opening 416 that is aligned with the second opening 414 and is spaced apart from the first opening 416 and 412 includes a first pin 412 that extends through the first openings 414, 416 and a second pin 412 that extends through the second openings 414, 416 such that the second pin 412 is spaced apart from the first pin 412.

As screw 326 is rotated about axis X1 in an opposite second rotational direction, screw 326 translates along axis X1 in the direction shown by arrow B in FIG. 3 such that member 318 moves along axis X1 in the direction shown by arrow B in FIG. 26 and member 320 translates along axis X1 in the direction shown by arrow B in FIG. 3, ramp 338 slides along ramp 340 and inclined surfaces 342 of member 320 slide along inclined surfaces 344 of plate 324 to simultaneously decrease the angle of implant 314 and the height of implant 314.

Core 316 extends along central longitudinal axis X1 between a distal end 350 and an opposite proximal end 360. Core 316 includes a wall 352 that defines thread 334. Tread 334 and an inner surface of wall 352 define a passageway 354. In some embodiments, passageway 354 is coaxial with axis X1. In some embodiments, passageway 354 may be disposed at alternate orientations, relative to axis X1, such as, for example, transverse and/or other angular orientations such as acute or obtuse and/or may be offset or staggered.

Wall 352 includes end sections 356, 358 and a middle section 362 positioned between section 356 and section 358. Section 356 is configured for disposal in a recess 364 of plate 322 prior to expansion of implant 314 such that a portion of a top surface 366 of wall 352 is flush or substantially flush with a vertebral engaging surface 368 of plate 322. That is, the portion of surface 366 that defines part of section 356 is flush or substantially flush with surface 368 of plate 322 prior to expansion of implant 314. Section 358 is configured for disposal in a gap 370 of plate 322 prior to angular expansion of implant 314 such that surface 366 is flush or substantially flush with surface 368. That is, the portion of surface 366 that defines part of section 358 is flush or substantially flush with surface 368 prior to expansion of implant 314. In some embodiments, section 356 includes spaced apart extensions 356a, 356b and recess 364 includes spaced apart recesses 364 each configured for disposal of one of extensions 356a, 356b. Section 362 is configured for disposal in a recess 372 of plate 322 prior to angular expansion of implant 314 such that surface 366 is flush or substantially flush with surface 368. That is, the portion of surface 366 that defines part of section 362 is flush or substantially flush with surface 368 prior to expansion of implant 314. In some embodiments, section 356, section, 358, section 362, recess 364, gap 370 and/or recess 372 can have various shape configurations, such as, for example, circular, oval, oblong, square, polygonal, irregular, uniform, non-uniform, variable and/or tapered.

Wall 352 includes end sections 374, 376 and a middle section 378 positioned between section 374 and section 376. Section 374 is configured for disposal in a recess 380 of plate 324 prior to expansion of implant 314 such that a portion of a bottom surface 382 of wall 352 is flush or substantially flush with a vertebral engaging surface 384 of plate 324. That is, the portion of surface 382 that defines part of section 374 is flush or substantially flush with surface 384 of plate 324 prior to expansion of implant 314. Section 376 is configured for disposal in a gap 386 of plate 324 prior to angular expansion of implant 314 such that surface 382 is flush or substantially flush with surface 384. That is, the portion of surface 382 that defines part of section 376 is flush or substantially flush with surface 384 prior to expansion of implant 314. Section 378 is configured for disposal in a recess 388 of plate 322 prior to angular expansion of implant 314 such that surface 382 is flush or substantially flush with surface 384. That is, the portion of surface 382 that defines part of section 378 is flush or substantially flush with surface 384 prior to expansion of implant 314. In some embodiments, section 374, section, 376, section 378, recess 380, gap 386 and/or recess 388 can have various shape configurations, such as, for example, circular, oval, oblong, square, polygonal, irregular, uniform, non-uniform, variable and/or tapered.

Member 318 is configured to translate relative to core 316 along axis X1 in opposite directions to selectively increase and decrease an angle of implant 314, as discussed herein. Screw 326 is configured for disposal in a passageway 390 of member 318 that is defined by thread 330 such that thread 328 engages thread 330. Rotation of screw 326 relative to core 316 about axis X1 in a first rotational direction, such as, for example, clockwise will translate member 318 relative to core 316 along axis X1 in a first axial direction, such as, for example, the direction shown by arrow A in FIG. 3 and rotation of screw 326 relative to core 316 about axis X1 in an opposite rotational direction, such as, for example, counterclockwise will translate member 318 relative to core 316 along axis X1 in an opposite section axial direction, such as, for example, the direction shown by arrow B in FIG. 3.

Figure 2:
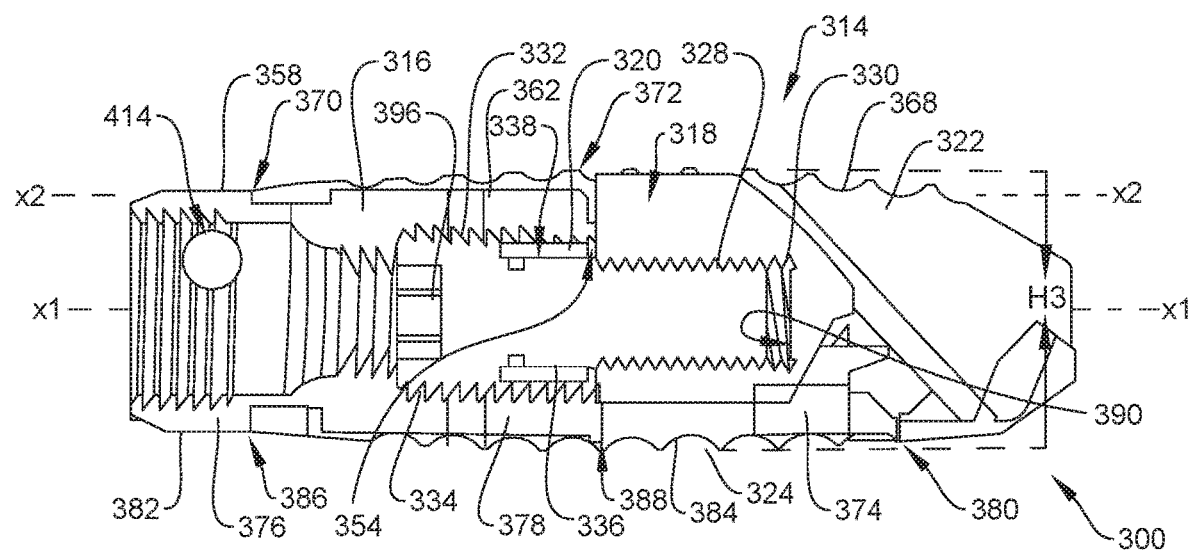
FIG. 2 is a side, cross-sectional view of the implant shown in FIG. 1.

As member 318 translates relative to core 316 along axis X1 in the direction shown by arrow A in FIG. 3, ramp 340 slides along ramp 342 to increase the angle of implant 314. For example, member 318 may be translated relative to core 316 along axis X1 in the direction shown by arrow A in FIG. 3 to move implant 314 from a first orientation in which a longitudinal axis X2 defined by plate 322 extends parallel to axis X1, as shown in FIGS. 1 and 2, to a second orientation in which axis X2 extends at an acute angle relative to axis X1, as shown in FIG. 3. A longitudinal axis X3 defined by plate 324 extends parallel to axis X1 as implant 314 moves between the first and second orientations. In some embodiments, ramp 340 includes a projection, such as, for example, a flange 392 that slides within a groove 394 of ramp 342 as implant 314 moves between the first and second orientations. In some embodiments, ramp 342 includes a projection, such as, for example, a flange that slides within a groove of ramp 340 as implant 314 moves between the first and second orientations.

As member 318 translates relative to core 316 along axis X1 in the direction shown by arrow B in FIG. 3, ramp 340 slides along ramp 342 to decrease the angle of implant 314. For example, member 318 may be translated relative to core 316 along axis X1 in the direction shown by arrow B in FIG. 3 to move implant 314 from the second orientation in which axis X2 extends at an acute angle relative to axis X1, as shown in FIG. 3, to the first orientation in which a longitudinal axis X2 defined by plate 322 extends parallel to axis X1, as shown in FIGS. 1 and 2.

Screw 326 includes a socket 396 configured for disposal of a bit of a driver configured to rotate screw 326 relative to core 316 about axis X1 in opposite directions, as discussed herein. In some embodiments, socket 396 includes a hex-alobe cross-sectional configuration configured for engagement with a bit of a driver having a hexalobe cross-sectional configuration to rotate screw 326. However, it is envisioned that socket 396 may include a square, triangular, polygonal, star cross sectional configuration configured engage a correspondingly shaped bit of a driver.

Member 320 is configured to translate relative to core 316 along axis X1 in opposite directions to selectively increase and decrease a height of implant 314, as discussed herein. Thread 332 engages thread 334 such that rotation of screw 326 relative to core 316 about axis X1 in a first rotational direction, such as, for example, clockwise will translate screw 326 along axis X1 and member 320 in a first axial direction, such as, for example, the direction shown by arrow A in FIG. 3 and rotation of screw 326 relative to core 316 about axis X1 in an opposite rotational direction, such as, for example, counterclockwise will translate screw 326 and member 320 along axis X1 in an opposite section axial direction, such as, for example, the direction shown by arrow B in FIG. 3.

As member 320 translates relative to core 316 along axis X1 in the direction shown by arrow A in FIG. 3, surfaces 344 slide along surfaces 346 to increase the height of implant 314, wherein the height of implant 314 is defined by the distance from surface 368 to surface 384. For example, member 320 may be translated relative to core 316 along axis X1 in the direction shown by arrow A in FIG. 3 to move implant 314 from a first configuration in which implant 314 has a first maximum height H1, as shown in FIGS. 1 and 2, to a second configuration in which implant 314 has an increased second height H2, as shown in FIG. 3. Axis X3 extends parallel to axis X1 as implant 314 moves between the first and second configurations.

As member 320 translates relative to core 316 along axis X1 in the direction shown by arrow B in FIG. 3, surfaces 344 slide along surfaces 346 to decrease the height of implant 314. For example, member 320 may be translated relative to core 316 along axis X1 in the direction shown by arrow B in FIG. 3 to move implant 314 from the second configuration in which implant 314 has height H2, as shown in FIG. 3, to the first configuration, in which implant 314 has height H1.

Member 320 includes an engagement portion 398 configured to engage screw 326 to couple screw 326 to member 320, as discussed herein. Portion 398 defines an opening 338. Opening 338 is configured for disposal of screw 326 such that screw 326 is rotatable relative to member 320, translation of screw 326 relative to core 316 along axis X1 in a first direction also translates member 320 relative to core 316 along axis X1 in the first direction and translation of screw 326 relative to core 316 along axis X1 in an opposite second direction also translates member 320 relative to core 316 along axis X1 in the second direction. In some embodiments, opening 338 can have various shape configurations, such as, for example, oval, oblong, polygonal, irregular, uniform, non-uniform, variable and/or tapered.

Member 320 includes an arm 400 extending from a first side of portion 398 and an arm 402 extending from a second side of portion 398. Arm 402 is spaced apart from arm 400 by portion 398. Arm 400 includes spaced apart extensions, such as, for example, flanges 404, 406 that extends outwardly from arm 400 and arm 402 includes spaced apart extensions, such as, for example, flanges 408, 410 that extends outwardly from arm 402. Flanges, 404, 406, 408, 410 define surfaces 344. In some embodiments, flanges 404, 406, 408, 410 each include a surface 344 and a surface 344 opposite the surface 344. That is, flanges 404, 406, 408, 410 each include a surface 344 and a surface 344 that faces away from the surface 344.

In operation and use, system 300 is employed with a surgical procedure, such as, a fusion treatment of a spine of a patient including vertebrae and body areas adjacent thereto, as discussed herein. System 300 may also be employed with other surgical procedures, such as, for example, discectomy, laminotomy, laminectomy, nerve root retraction, foramenotomy, facetectomy, decompression, and spinal, nucleus or disc replacement.

For example, system 300 can be employed with a surgical arthrodesis procedure, such as, for example, an interbody fusion for treatment of an applicable condition or injury of an affected section of a spinal column and adjacent areas within a body, such as, for example, an intervertebral disc space between a first vertebra and a second vertebra. It is contemplated that intervertebral implant 314 of system 300, described above, can be inserted within the intervertebral disc space to space apart articular joint surfaces, provide support and maximize stabilization of the vertebrae. It is further contemplated that intervertebral implant 314 provides height restoration between vertebral bodies, decompression, restoration of sagittal balance and/or resistance of subsidence into vertebral endplates.

In use, to treat the affected section of the vertebrae, a medical practitioner obtains access to a surgical site including the vertebrae in any appropriate manner, such as through incision and retraction of tissues. It is envisioned that system 300 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure is performed for treating the spine disorder. Intervertebral implant 314, described above, is then employed to augment the surgical treatment. Intervertebral implant 314 can be delivered or implanted as a pre-assembled device or can be assembled in situ. Intervertebral implant 314 can be completely or partially revised, removed or replaced in situ. It is contemplated that one or all of the components of the interbody implant system can be delivered to the surgical site via manual manipulation and/or a free hand technique. It is further contemplated that intervertebral implant 314 may be inserted posteriorly, and then manipulated anteriorly and/or lateral and/or medial.

An incision is made in the body of a patient and a cutting instrument creates a surgical pathway for implantation of intervertebral implant 314 within the patient body. A guide instrument is employed to initially distract the first vertebra from the second vertebra. A sleeve or cannula is used to access the intervertebral disc space and facilitate delivery and access for components of the interbody implant system. A preparation instrument can be inserted within the sleeve or cannula and disposed within the intervertebral disc space. The preparation instrument(s) can be employed to remove some or all of the disc tissue including the disc nucleus and fluids, adjacent tissues and/or bone, corticate, scrape and/or remove tissue from the surfaces of endplates of the first and second vertebrae, as well as for aspiration and irrigation of the region according to the requirements of a particular surgical application.

Implant 314 is inserted into the patient using an instrument, such as, for example, an inserter, with implant 314 disposed in an undeployed or unexpanded configuration, as shown in FIGS. 1 and 2. Implant 314 is delivered along the surgical pathway using a substantially posterior approach to position implant 314 within the intervertebral disc space.

Upon desired positioning of intervertebral implant 314 within the intervertebral disc space, implant 314 is deployed within the intervertebral disc space to move implant 314 from the undeployed or unexpanded configuration, shown in FIGS. 1 and 2 in which implant 314 has height H1 and axis X2 extends parallel to axis X1, to a deployed or expanded configuration, shown in FIG. 3, in which the height and angle of implant 314 is increased such that implant has height H2 and axis X2 extends at an acute angle relative to axis X1. Implant 314 is moved from the undeployed or unexpanded configuration to the deployed or expanded configuration by inserting a bit of a driver in socket 396 such that the bit mates with socket 396 and rotation of the driver also rotates screw 326. The driver is rotated in a first rotational direction such that screw 326 translates relative to core 316 along axis X1 in the direction shown by arrow A in FIG. 3 such that screw 326 translates members 318, 320 relative to core 326 along axis X1 in the direction shown by arrow A in FIG. 3. As member 318 translates relative to core 316 along axis X1 in the direction shown by arrow A in FIG. 3, ramp 340 slides along ramp 342 to increase the angle of implant 314. As member 320 translates relative to core 316 along axis X1 in the direction shown by arrow A in FIG. 3, surfaces 344 slide along surfaces 346 to increase the height of implant 314.

As implant 314 moves from the undeployed or unexpanded configuration to the deployed or expanded configuration, surface 368 moves away from surface 384 such that surfaces 368, 384 push against the vertebrae to move the first vertebra away from the second vertebra and increase the size of the intervertebral disc space. It is contemplated that in the deployed or expanded configuration, intervertebral implant 314 provides height restoration between the first vertebra and the second vertebrae, decompression, restoration of sagittal balance and resistance of subsidence into the endplates of the vertebrae. Implant 314 may be kept in the deployed or expanded configuration to maintain the increased size of the intervertebral disc space. In some embodiments, a material, such as, for example, bone graft is inserted into implant 314 to promote bone growth to fuse the first vertebra with the second vertebra.

In some embodiments, the bone graft can be a particulate material, which may include an osteoconductive material such as HA and/or an osteoinductive agent such as a bone morphogenic protein (BMP) to enhance bony fixation of intervertebral implant 314 with the adjacent vertebrae. It is contemplated that the bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Intervertebral implant 314 can be made of radiolucent materials such as polymers. Radiomarkers may be included for identification under x-ray, fluoroscopy, CT or other imaging techniques. It is envisioned that the bone graft may include one or a plurality of therapeutic agents and/or pharmacological agents for release, including sustained release, to treat, for example, pain, inflammation and degeneration.

It is envisioned that the components of system 300, which may include one or a plurality of intervertebral implants 314, can be delivered to the surgical site via alternate approaches. In one embodiment, intervertebral implant 314 is delivered through the surgical pathway along a transforaminal lumbar interbody fusion approach into the intervertebral disc space and disposed in the deployed or expanded configuration. In one embodiment, a plurality of intervertebral implants 314 are delivered through the surgical pathway along a posterior lumbar interbody fusion approach into the intervertebral disc space and disposed in the deployed or expanded configuration in a side by side orientation.

In some embodiments, intervertebral implant 314 can be expanded from the undeployed or unexpanded configuration to alternate configurations between the undeployed or unexpanded configuration and the deployed or expanded configuration. In some embodiments, intervertebral implant 314 can be collapsed from the deployed or expanded configuration to alternate configurations between the deployed or expanded configuration and the undeployed or unexpanded configuration.

Implant 314 may be moved from the deployed or expanded configuration to the undeployed or unexpanded configuration by inserting the bit of the driver in socket 396 such that the bit mates with socket 396 and rotation of the driver also rotates screw 326. The driver is rotated in an opposite rotational direction such that screw 326 translates relative to core 316 along axis X1 in the direction shown by arrow B in FIG. 3 such that screw 326 translates members 318, 320 relative to core 326 along axis X1 in the direction shown by arrow B in FIG. 3. As member 318 translates relative to core 316 along axis X1 in the direction shown by arrow B in FIG. 3, ramp 340 slides along ramp 342 to decrease the angle of implant 314. As member 320 translates relative to core 316 along axis X1 in the direction shown by arrow B in FIG. 3, surfaces 344 slide along surfaces 346 to decrease the height of implant 314. Once implant 314 is in the undeployed or unexpanded configuration, implant 314 can be moved within the intervertebral disc space and/or removed from the intervertebral disc space, as desired.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device to space apart vertebral members, the device comprising:
    a core extending along a longitudinal axis between opposite proximal and distal ends, the core defining a first female thread;
    a drive screw including opposite first and second ends, the first end including a first male thread, the second end including a second male thread, the second male thread engaging the first female thread;
    a first body comprising a second female thread, the first body being coupled to the first end such that the first male thread engages the second female thread;
    a second body coupled to the drive screw;
    a first plate coupled to the core and the first body, the first plate comprising a first vertebral engaging surface; and
    a second plate coupled to the core, the second plate comprising a second vertebral engaging surface,
    wherein the drive screw is configured to rotate relative to the core to simultaneously pivot the first plate relative to the core and alter a distance between the first vertebral engaging surface and the second vertebral engaging surface, and
    wherein the second plate comprises a plurality of first inclined surfaces, the second body comprising a plurality of second inclined surfaces, the second inclined surfaces being configured to slide along the first inclined surfaces to alter the distance between the first vertebral engaging surface and the second vertebral engaging surface.

2. The device recited in claim 1, wherein the first body comprises a first ramp, the first plate comprises a second ramp, the second ramp being configured to slide along the first ramp to pivot the first plate relative to the core.

3. The device recited in claim 1, wherein the second female thread is a left-handed thread and the first female thread is a right-handed thread.

4. The device recited in claim 1, wherein the first male thread and the second female thread are left-handed threads and the second male thread and the first female thread are right-handed threads.

5. The device recited in claim 1, wherein the first female thread has a major diameter that is less than a major diameter of the second female thread.

6. The device recited in claim 1, wherein at least one of the core, the first body, the second body, the first plate, the second plate is made from polyether ether ketone.

7. The device recited in claim 1, wherein the drive screw includes an unthreaded portion between the first male thread and the second male thread, the unthreaded portion being positioned in an opening of the second body such that the drive screw is rotatable relative to the second body and translation of the drive screw along the longitudinal axis translates the second body along the longitudinal axis.

8. The device recited in claim 7, wherein the opening is circular.

9. The device recited in claim 1, wherein rotation of the drive screw relative to the core in a first direction moves the device from a first configuration in which the vertebral engaging surfaces extend parallel to the longitudinal axis and are spaced apart from one another by a first distance to a second configuration in which the first vertebral engaging surface extends at an acute angle relative to the longitudinal axis and the vertebral engaging surfaces are spaced apart from one another by an increased second distance.

10. The device recited in claim 9, wherein the first body moves toward the second body as the device moves from the first configuration to the second configuration.

11. The device recited in claim 9, wherein rotation of the drive screw relative to the core in an opposite direction moves the device from the second configuration to the first configuration.

12. The device recited in claim 9, wherein the first female thread defines a cavity, the cavity having a first volume when the device is in the first configuration, the cavity having an increased second volume when the device is in the second configuration.

13. The device recited in claim 9, wherein the second vertebral engaging surface extends parallel to the longitudinal axis when the device is in the second configuration.

14. The device recited in claim 9, wherein a projection of the first body slides within a groove of the first plate as the device moves between the first and second configurations.

15. The device recited in claim 9, wherein the longitudinal axis is a first longitudinal axis, the second female thread defining a passageway, the passageway extending along a second longitudinal axis, the second longitudinal axis being coaxial with the first longitudinal axis as the device moves between the first and second configurations.

16. The device recited in claim 9, wherein the longitudinal axis is a first longitudinal axis, the second body extending along a second longitudinal axis, the second longitudinal axis being parallel to the first longitudinal axis as the device moves between the first and second configurations.

17. The device recited in claim 1, wherein the first plate is coupled to the core by a pin such that the first plate is pivotable relative to the core about the pin.

18. A device to space apart vertebral members, the device comprising:
a core extending along a longitudinal axis between opposite proximal and distal ends, the core defining a first female thread;
a drive screw including opposite first and second ends, the first end including a first male thread, the second end including a second male thread, the second male thread engaging the first female thread;
a first body comprising a second female thread, the first body being coupled to the first end such that the first male thread engages the second female thread;
a second body coupled to the drive screw;
a first plate coupled to the core and the first body, the first plate comprising a first vertebral engaging surface; and
a second plate coupled to the core, the second plate comprising a second vertebral engaging surface,
wherein the drive screw is configured to rotate relative to the core to simultaneously pivot the first plate relative to the core and alter a distance between the first vertebral engaging surface and the second vertebral engaging surface, and
wherein the first female thread has a major diameter that is less than a major diameter of the second female thread.

19. The device recited in claim 18, wherein the second female thread is a left-handed thread and the first female thread is a right-handed thread.

20. A device to space apart vertebral members, the device comprising:
a core extending along a longitudinal axis between opposite proximal and distal ends, the core defining a first female thread;
a drive screw including opposite first and second ends, the first end including a first male thread, the second end including a second male thread, the second male thread engaging the first female thread;
a first body comprising a second female thread, the first body being coupled to the first end such that the first male thread engages the second female thread;
a second body coupled to the drive screw;
a first plate coupled to the core and the first body, the first plate comprising a first vertebral engaging surface; and
a second plate coupled to the core, the second plate comprising a second vertebral engaging surface,
wherein the drive screw is configured to rotate relative to the core to simultaneously pivot the first plate relative to the core and alter a distance between the first vertebral engaging surface and the second vertebral engaging surface, and
wherein the drive screw includes an unthreaded portion between the first male thread and the second male thread, the unthreaded portion being positioned in an opening of the second body such that the drive screw is rotatable relative to the second body and translation of the drive screw along the longitudinal axis translates the second body along the longitudinal axis.

* * * * *